US 6,605,091 B1

(12) United States Patent
Iwanski (10) Patent No.: US 6,605,091 B1
(45) Date of Patent: Aug. 12, 2003

(54) SURGICAL CABLE ASSEMBLY AND METHOD

(75) Inventor: George J. Iwanski, Marquette, MI (US)

(73) Assignee: Pioneer Laboratories, Inc., Marquette, MI (US)

( * ) Notice: Subject to any disclaimer, the term of this patent is extended or adjusted under 35 U.S.C. 154(b) by 131 days.

(21) Appl. No.: 09/608,536

(22) Filed: Jun. 30, 2000

(51) Int. Cl.$^7$ ................................................ A61B 17/56
(52) U.S. Cl. ........................................................ 606/74
(58) Field of Search ................ 606/74, 103; 24/129 W, 24/115 H, 115 K, 132

(56) References Cited

U.S. PATENT DOCUMENTS

| | | | |
|---|---|---|---|
| 2,509,272 A | 5/1950 | Karnuth et al. ............... 244/49 |
| 3,111,945 A | 11/1963 | Von Solbrig ................. 128/92 |
| 3,507,270 A | 4/1970 | Ferrier ....................... 128/2.05 |
| 3,570,497 A | 3/1971 | Lemole .................... 128/335.5 |
| 3,709,218 A | 1/1973 | Halloran .................... 128/92 A |
| 3,802,438 A | 4/1974 | Wolvek ........................ 128/335 |
| 3,840,018 A | 10/1974 | Heifetz ........................ 128/346 |
| 3,997,138 A | 12/1976 | Crock et al. ................ 248/67.5 |
| 4,047,523 A | 9/1977 | Hall .............................. 128/69 |
| 4,047,524 A | 9/1977 | Hall .............................. 128/69 |
| 4,119,091 A | 10/1978 | Partridge .................... 128/92 B |
| 4,128,100 A | 12/1978 | Wendorff .................. 128/335.5 |
| 4,146,022 A | 3/1979 | Johnson et al. ............ 128/92 B |
| 4,269,180 A | 5/1981 | Dall et al. ................. 128/92 B |
| 4,535,764 A | 8/1985 | Ebert ......................... 128/92 B |
| 4,587,963 A | 5/1986 | Leibinger et al. ......... 128/92 B |
| 4,667,662 A | 5/1987 | Titone et al. ........... 128/92 YD |
| 4,790,303 A | 12/1988 | Steffee ................... 128/924 M |
| 4,813,416 A | 3/1989 | Pollak et al. ................. 128/335 |
| 4,889,110 A | 12/1989 | Galline et al. ................. 606/69 |
| 4,966,600 A | 10/1990 | Songer et al. ................. 606/74 |
| 5,116,340 A | 5/1992 | Songer et al. ............... 606/103 |
| 5,123,456 A | 6/1992 | Jansen ......................... 140/93.4 |
| 5,312,410 A | 5/1994 | Miller et al. ................... 606/86 |
| 5,395,374 A | 3/1995 | Miller et al. ................... 606/74 |
| 5,415,658 A | 5/1995 | Kilpela et al. ................. 606/57 |

(List continued on next page.)

FOREIGN PATENT DOCUMENTS

| | | |
|---|---|---|
| AU | 126455 | 1/1948 |
| CA | 548197 | 10/1957 |
| CH | 425 604 | 11/1966 |
| DE | 26 44 735 | 4/1977 |
| DE | 29 11 748 | 10/1980 |
| DE | 31 46 634 A1 | 6/1983 |
| DE | 32 44 680 A1 | 6/1984 |
| DE | 40 24 334 A1 | 2/1992 |
| FR | 543126 | 8/1922 |
| GB | 2 207 055 A | 1/1989 |
| NL | 7610576 | 9/1976 |

OTHER PUBLICATIONS

Zimmer, Inc. product literature entitled "Cable–Ready® Long GTR Device", 1997.

(List continued on next page.)

Primary Examiner—John J. Wilson
(74) Attorney, Agent, or Firm—Fitch, Even, Tabin, & Flannery (57) ABSTRACT

A surgical cable assembly is provided for securing bones, or securing medical implant devices to bones. The assembly preferably comprises a multistrand metal cable and a crimpable coupling member attached to a loop in the cable adjacent one end formed by a separate crimp member. The coupling member secures the cable in a permanent loop that encircles the bone and is capable of pivoting to permit the cable to follow the outer contour of the bone and/or implant. The coupling member may comprise a flange to limit its rotation about the cable. A method of securing bones and/or implants with the cable assembly also is provided.

22 Claims, 5 Drawing Sheets

U.S. PATENT DOCUMENTS

| | | | |
|---|---|---|---|
| 5,423,820 A | 6/1995 | Miller et al. | 606/74 |
| 5,476,465 A | 12/1995 | Preissman | 606/61 |
| 5,569,253 A | 10/1996 | Farris et al. | 606/74 |
| 5,772,663 A | 6/1998 | Whiteside et al. | 606/74 |
| 5,928,237 A | 7/1999 | Farris et al. | 606/74 |
| 6,077,268 A | 6/2000 | Farris et al. | 606/74 |
| 6,086,590 A * | 7/2000 | Margulies et al. | 606/74 |

OTHER PUBLICATIONS

Zimmer, Inc. product literature entitled "Cable–Ready Cable Grip System", Aug. 1994.

Howmedica product literature entitled "The Dall–Miles Trochanter Cable Grip System", Feb. 1991.

* cited by examiner

SURGICAL CABLE ASSEMBLY AND METHOD

FIELD OF THE INVENTION

The present invention relates to an apparatus and method for securing body parts with a surgical cable. In particular, the invention relates to a surgical cable assembly that includes a flexible cable that can be wrapped around body parts, such as bones, and a rotating crimpable coupling for securing the flexible cable in a closed loop about the bone.

BACKGROUND OF THE INVENTION

Surgical cables are used in various surgical procedures, for example, to fix fractured bones or to secure an implant to a bone. The cable may be a monofilament wire or multifilament cable. Typically, the cable is used to encircle the broken bone and hold it together as it heals or to hold an implant device in position next to a bone.

The configuration of the surgical cable assembly may impact the ease with which the cable is installed. A typical surgical cable assembly may include the cable and one or more pieces for securing the cable in a loop under tension, such as a stop to fix the ends of the cable to form the tensioned loop. One known type of cable assembly utilizes a small, permanent loop at one end, formed by a first crimp member. The opposite free end of the cable is wrapped around the bone and threaded through the small loop during the surgical procedure. The resulting second loop formed around the bone is then secured by sliding a loose tubular crimp member along the cable to the small permanent loop and crimping the tubular member with a crimping tool. Examples of such assemblies are disclosed in U.S. Pat. Nos. 4,966,600 and 5,116,340.

Given the need to limit the intrusiveness of the cable assembly within the surgical site and the desire to limit the size of the incision, such cable assemblies and associated components tend to be small and therefore difficult for a surgeon to handle. In particular, the task of threading the cable through the aperture in the small loose tubular member during surgery may be difficult for a surgeon wearing gloves. Further, the requirement that the surgeon account for all items used during surgery makes the use of small, loose pieces that may be readily dropped undesirable.

Installation of surgical cables may be frustrated by factors such as the difficulties encountered by the surgeon in having to handle the various devices and implements required for installation of a cable assembly. For example, one or more tools to tension the cable and/or temporarily hold the cable, to crimp the cable crimp, and to cut the cable may be used during installation of the surgical cable. The surgeon must be able to manipulate these various tools while installing the cable assembly. The physical constraints of the surgical site also may impact the ease with which a surgical cable assembly is installed. Access to the surgical site may be obstructed due to the particular location of the body where the cable is being installed or may be limited as a result of the desire to limit the size of the incision. Thus, the surgeon may experience difficulties in working with a number of tools in a small area while trying to position, tighten and fix the cable assembly about the bone, such that it may not be possible to readily achieve the desired tension and effectively maintain it until the cable is secured.

Another type of cable assembly is secured by a single L-shaped crimp member having two crimp able portions. One end portion of the cable is immovably fixed in the first crimp able portion. The opposite end of the cable is threaded around the bone and then fixed in the second crimp able portion. With this assembly, the surgeon does not have to handle a separate, loose crimp member. To form the cable loop, the surgeon only has to thread the opposite end of the cable through a second aperture in the crimp. Such an assembly is disclosed in U.S. Pat. No. 5,423,820 to Miller, et al.

When installing a cable assembly, it is desirable to obtain a predetermined amount of tension in the cable loop so that the cable is properly mechanically fixed around the bone. It is thus important to avoid formation of slack in the loop as the surgical installation is being completed. To limit slack, it is desirable to tighten the cable so that the cable generally conforms to the shape of the bone and fits snugly around the bone. The strength of a cable loop is also greater when the two ends of the cable are positioned essentially parallel to one another in a plane tangent to the surface of the bone. Because the ends of the cable disclosed in Miller, et al. are oriented perpendicular to one another as a result of the configuration of the L-shaped crimp, it may not be possible to have both ends flush with the surface of the bone. With both cable ends fixed in the Miller, et al. assembly in the L-shaped crimp, the crimp cannot rotate or pivot in any direction without forming sharp bends in the cable. Moreover, the L-shaped crimp of Miller, et al. may protrude into adjacent tissue and cause the cable loop to be lifted away from the bone along a length of the loop which also may reduce its strength.

U.S. Pat. Nos. 5,928,237 and 5,569,253 disclose cable assemblies utilizing two crimps, the crimps being held in ball and socket or ball and seat abutment to allow them to swivel relative to each other. One drawback of these assemblies is the complex machining required to fabricate the relatively small ball and socket or ball and seat joints. A further drawback is that in use, the swivel action of the joint may prevent holding the cable loop roughly in a single plane and result in twisting and bending of the cable. The swivel action between the crimps may also make the task of locating the second crimp aperture and threading the free cable end through the crimp aperture difficult during surgery.

Thus it is desirable to have a surgical cable assembly that may be readily handled by a surgeon and easily installed during surgery to form a secure cable loop about a bone. It is also desirable to have such a surgical cable assembly that may be orientated to facilitate tensioning of the loop to avoid formation of slack, cable twisting, and sharp cable bends. The cable assembly should be easy to manufacture, compact, and only minimally intrusive in the body.

SUMMARY OF THE INVENTION

In accordance with the present invention, an apparatus and method are provided for securing body parts, such as bones. A surgical cable assembly for encircling a bone comprises a length of cable that has first and second ends and a coupling member which has a shoulder portion having a first aperture extending therethrough. A small, preformed loop near the first end of the cable has a portion loosely received in the shoulder aperture. The coupling member also has a second part, or neck portion. The neck portion has a second aperture extending through a malleable portion configured to be crimped about the flexible cable for fixing the coupling along the flexible cable so as to secure the surgical cable assembly around the bone.

The portion of cable extending through the shoulder aperture forms an axis of rotation for the coupling member.

With the coupling member rotatably mounted about a portion of the small cable loop, the second end of the flexible cable is passable through the second aperture to loop the flexible cable around the bone at a desired orientation. Because the small loop adjacent the first cable end is not fixed (i.e., crimped) in the shoulder aperture, the angle of the neck portion of the coupling member relative to the bone surface may be adjusted to achieve the desired tension, strength and orientation of the cable assembly around the bone by pivoting the coupling member about the preformed loop. Once the cable is looped around the bone, the neck of the coupling member is fixed at a position along the flexible cable by crimping to maintain a predetermined tension of the loop and secure the loop in a desired position around the bone.

A separate loop crimp member secures the first end of the flexible cable back along the length of the flexible cable to form the small, permanent loop adjacent the first end of the flexible cable. The flexible cable is rotatably attached to the first part through the first aperture by the connecting loop. The coupling member may also comprise a flange for controlling the degree of rotation of the coupling member around the small preformed loop.

A method of securing a bone with a surgical cable assembly includes first providing a surgical cable assembly that comprises a coupling member having a shoulder portion with a first aperture extending therethrough, a neck portion having a second aperture extending therethrough, and a flexible cable having first and second ends spaced by a length, where the coupling member is rotatably mounted on a small cable loop adjacent the first end by means of the first aperture.

The method further comprises passing the second end of the flexible cable around the bone and through the second aperture of the coupling member to form a loop of the flexible cable around the bone. The loop is then tightened to a desired tension about the bone. A suitable tensioning tool may be used for this purpose. Depending on the contour of the bone surface and the desired tension, the tensioning step may involve pivoting the coupling member relative to the small loop threaded through the first aperture.

The neck of the coupling member is crimped to secure it about the flexible cable at a point along the cable length necessary to maintain the desired loop tension and desired angle of the neck of the coupling member relative to the bone surface. After the coupling member is crimped, the flexible cable is cut essentially flush with the end of the neck portion, at the end opposite the cable loop.

In the preferred method, the coupling member is provided pre-mounted on the small cable loop by passing the first cable end through the first aperture of the coupling and then securing it back against a length of the flexible cable so as to form the small loop. A separate tubular member is crimped about the first end of the flexible cable and the length of flexible cable along which the end is doubled back so as to fix the first end and form the preformed loop.

The method also may include passing the flexible cable around a medical implant or graft positioned adjacent the bone in order to secure the medical implant or graft against the bone.

DETAILED DESCRIPTION OF THE PREFERRED EMBODIMENT

Figure 1:
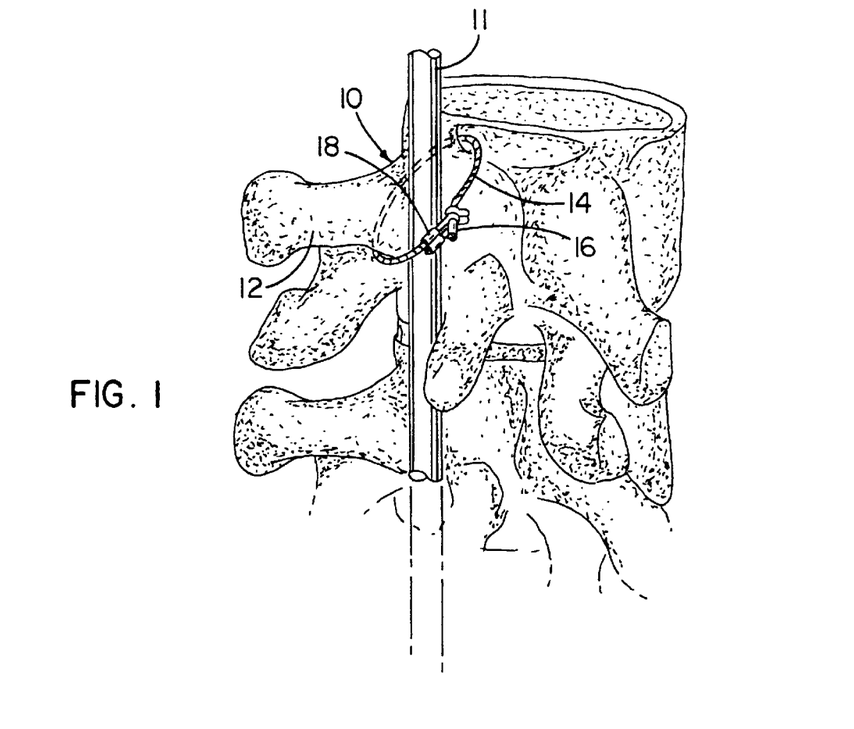
FIG. 1 is a schematic view of a surgical cable assembly secured around a portion of a spinal column and holding a medical implant against the spinal column in accordance with the present invention.

Referring to FIG. 1, there is illustrated a surgical cable assembly embodying features of the present invention. The preferred surgical cable assembly 10 may be used for securing a bone 12. The surgical cable assembly 10 generally comprises a flexible cable 14, a coupling member 16 and a loop crimp member 18. The coupling member 16 is pivotably mounted on a looped portion of the flexible cable 14 prior to use, and, during surgery, the free end of the cable 14 is passed around the subject bone and through an aperture in the coupling member 16 to form a closed loop around the subject bone 12. The surgical cable assembly 10 also may be used to hold a medical implant device 11, such as a splint, rod, graft or the like, against the bone 12.

Figure 2:
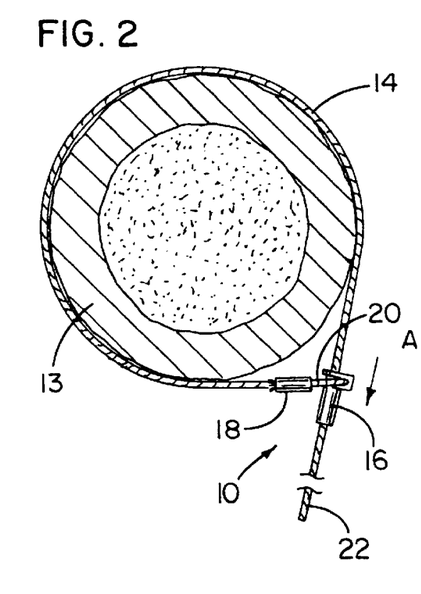
FIG. 2 is a cross-sectional view of the surgical cable assembly of FIG. 1 loosely encircling a different bone.
Figure 3:
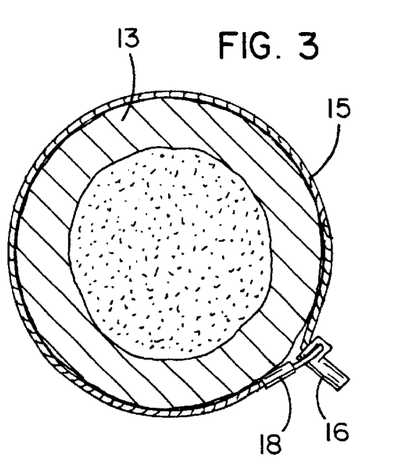
FIG. 3 is a view similar to FIG. 2 showing the surgical cable assembly secured to a desired tension around the bone.

As shown in FIGS. 2–3, one or more of the surgical cable assemblies 10 may be used to secure and provide reinforcement for a fractured bone 13 at the site of the fracture. Once positioned around the bone 13, the cable loop 15 is tightened to a desired tension to secure the cable assembly 10 closely around the bone 13 (FIG. 3).

The cable 14 is a surgical grade stainless steel, titanium alloy, or the like. Other materials such as cobalt chromium alloy or other suitable metals also may be used. In the preferred embodiment, the cable 14 is made of twisted multi strand stainless steel cable. In one form of the invention, as an example, the cable 14 has a diameter of between about 0.04 and 0.05 inches and more preferably about 0.043 inches. The cable 14 may be swedged to reduce surface roughness and may have a high flexibility, which may provide a tighter loop to hold the bone yet avoid damage to surrounding tissue. A stiffened leader may be used at the free end 22 of the cable 14 to facilitate threading of the cable 14 through the aperture in coupling member 16 during installation.

Figure 4:
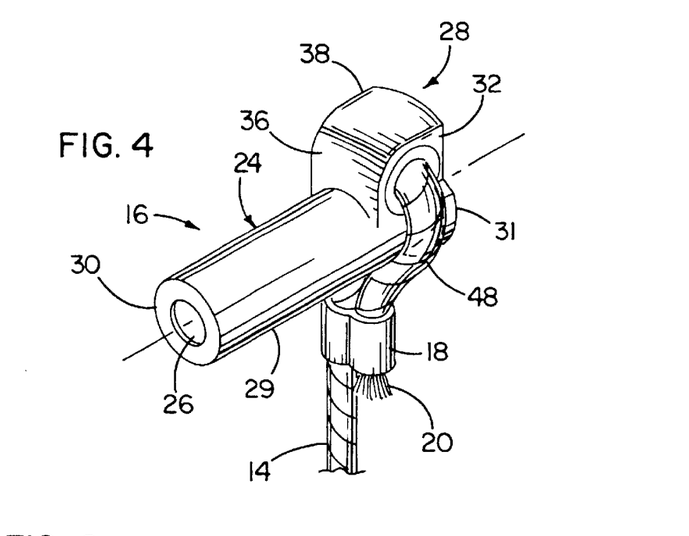
FIG. 4 is an enlarged perspective view of the crimp able coupling member and separate loop crimp in accordance with the present invention.
Figure 5:
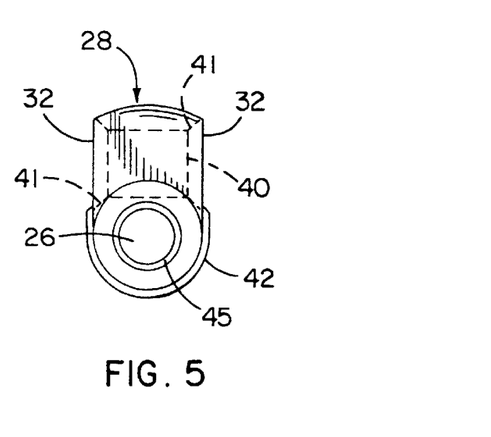
FIG. 5 is a front end elevational view of the crimp able coupling member of FIG. 4.
Figure 6:
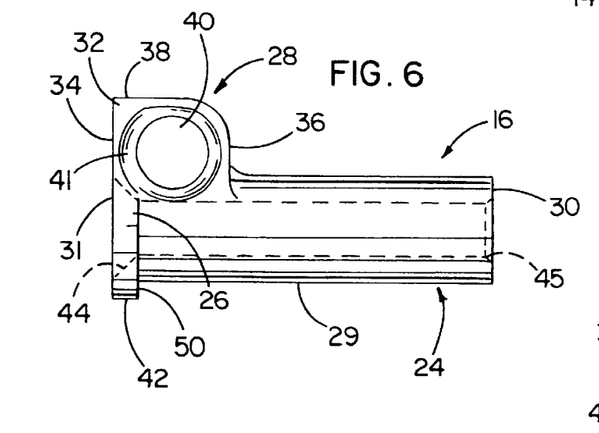
FIG. 6 is a left side elevational view of the crimp able coupling member of FIG. 4.

With reference now to FIGS. 4–6, the coupling member 16 is permanently, rotatably mounted about the preformed loop 48 adjacent the fixed end portion 20 of cable 14. The coupling member 16 comprises an elongated tubular neck portion 24 and a shoulder portion 28 extending from the neck portion 24. The coupling member 16 may be fabricated from a surgical grade stainless steel, titanium, titanium alloy, or the like, or cobalt chromium alloy or other malleable metals.

The neck portion 24 has a generally circular cross-section defined by a tubular wall 29. The inner surface of wall 29 defines an aperture 26 extending longitudinally therethrough from a first end 30 to a second end 31. The diameter of the aperture 26 preferably should be sized to allow the cable 14 to slide relatively freely through the aperture 26 when the assembly 10 is being installed. The aperture 26 also is sized to provide a compression fit between the inner surface of wall 29 and the cable 14 when the neck portion 24 is crimped to maintain the positioning of the cable 14 and secure the assembly 10. Using a 0.043 inch cable, as an example, the diameter of the aperture 26 may be about 0.044 and 0.053 inches and, more preferably, about 0.046 inches.

The outer circumference of the aperture 26 at the second end 31 preferably has a chamfered edge 44, such that the walls of the aperture 26 taper inwardly from the end 31 to a predetermined point at the interior of the neck portion, along a length of the aperture 26. The chamfered surface 44 facilitates insertion of the cable 14 through the aperture 26 by increasing the diameter of the aperture 26 at the second end 31. The chamfered edge 44 also allows the cable 14 to bend more gradually around the second end 31 of the neck portion 24, and avoids forming a sharp cable bend at that point as the cable 14 is pulled through the coupling member 16 and tightened. The outer circumference at the first end 30 also may have a chamfered edge 45 to avoid the formation of sharp bends in the cable while it is being tightened and to avoid fraying the cable.

The neck portion 24 is crimped along its length between shoulder portion 28 and the first end 30 when it is desired to secure the coupling member 16 at a position on the cable 14. The wall 29 of the neck portion 24 is sufficiently thin and malleable to allow the neck portion 24 to be readily crimped about the cable 14 using any crimping tool known in the art. It is generally desirable to minimize the size of the neck portion to limit the intrusiveness of the cable assembly into surrounding tissue. However, the neck portion 24 should be of sufficient length to provide access for a crimping tool and to provide sufficient crimping area to fixedly secure the coupling member 16 about the cable 14. In one example, the length of the neck portion 24 between the shoulder portion 28 and the first end 30 is about 0.23 inches.

The shoulder portion 28 of coupling member 16 extends outwardly from the neck portion 24 at the second end 31, is generally box-like in shape, and comprises two opposite side surfaces 32, a back surface 34, a front surface 36, and an upper surface 38. In one form of the invention, the two generally planar opposing side walls 32 extend tangentially from the outer surface of the neck 24 to provide sufficient clearance with the small permanent loop 48 about which coupling member 16 is mounted. The generally planar back surface 34 spans between the side surfaces 32, and the front surface 36 is opposite the back surface 34 and spans between the two side surfaces 32. As shown, the top surface 38 is preferably convex, with a radius of curvature that rotates about an axis parallel to the central longitudinal axis of the neck aperture 26. This further avoids interference with the small loop 48. However, the top surface 38 also may be planar or otherwise suitably configured.

An aperture 40 extends transversely through the shoulder portion 28 of coupling member 16 between the opposite side surfaces 32. The aperture 40 is positioned above the neck aperture 26 and has a central longitudinal axis perpendicular to a central longitudinal axis of the neck aperture 26. The aperture 40 has chamfered edges 41 at each of the two side surfaces 32 to minimize cable fraying. The small permanent loop 48 extends through aperture 40 and provides an axis of rotation of coupling member 16. The diameter of the aperture 40 is sufficiently greater than the diameter of the cable 14 to allow coupling member 16 to rotate freely about the permanent loop 48 of the cable 14. As an example, a shoulder portion aperture with a 0.061 inch diameter has been used effectively with a 0.043 inch diameter cable. Preferably, the dimensions of the shoulder portion 28 are just large enough to accommodate the aperture 40 and provide a sufficiently strong support structure for attaching the permanent loop 48 of the cable 14 to the coupling member 16.

The surgical cable assembly 10 is preassembled to have the coupling member 16 permanently mounted at the shoulder portion 28 about the permanent loop 48 of the cable 14. This is done by passing cable 14 through the aperture 40 and around the neck portion 24 to form the small loop 48 encircling the neck portion 24. A loop crimp member 18 is positioned along the cable 14 adjacent the coupling member 16 to secure the end portion 20 of the cable 14 and form the small loop 48. The end portion 20 of the cable is positioned within the loop crimp member 18 to temporarily form the small loop 48. Once the small loop 48 is formed, crimping the member 18 at one or more locations along its length permanently secures the small loop 48 around the coupling member 16.

As shown in FIG. 4, the loop crimp member 18 may be in the form of a double-lumen crimp that provides generally separate passages for each of the two cable portions extending therethrough. The double-lumen crimp member 18 limits slippage of fixed end 20 against the opposite portion of the cable 14 in the crimp member 18 as the larger cable loop 15 is tightened about the bone, thereby increasing the strength of the small loop 48. The crimp member 18 also may be generally circular in cross-section or otherwise shaped to accommodate two segments of the cable 14 therein. Moreover, the invention is not limited to embodiments in which the fixed end 20 is secured by a crimp. Any other type of fastener capable of securing the fixed end under tension may be used.

The small cable loop 48 may have a generally tear drop shape and should be sufficiently large enough to allow the coupling member 16 to pivot about the axis of rotation provided by the portion of the cable that extends through aperture 40. The rotation of the coupling member 16 about the loop 48 facilitates tensioning of the cable loop 15. When the neck portion of coupling member 16 is oriented perpendicular to the loop crimp member 18 and the free end 22 of the cable 14 is passed through the aperture 26, that portion of cable 14 is also generally perpendicular to the small loop 48, as shown in FIG. 2. In order to reduce the generally triangular space that remains between the cable assembly and the bone shown in FIG. 2, the coupling member must be allowed to pivot toward the loop crimp member 18. In the cable assembly of the present invention, as the cable loop 15 is tightened further around the subject bone 13, the neck portion 24 rotates about the small loop 48 and toward the loop crimp member 18 such that the neck portion becomes positioned at an acute angle relative to the loop crimp member 18. As the neck portion 24 rotates, the portion of the cable extending around the bone adjacent the loop crimp member 18 becomes oriented generally parallel to the portion of cable extending through and adjacent the coupling member 16. This orientation enables a tighter fit of cable assembly around the bone and provides greater cable loop 15 strength relative to a cable loop in which the two opposite end portions of cable are oriented essentially perpendicular to each other. At the same time, when oriented in a direction generally more tangent to, rather than extending radially out from, the bone 13, the coupling member 16 and any portion of the cable 14 that may project from the neck portion 24 are less likely to damage surrounding tissue. Other bone shapes may call for different degrees of rotation of the coupling member 16 about the loop 48.

The configuration of the small loop 48 and loop crimp member 18 to secure the coupling member 16 of the cable assembly provides further advantages in terms of the strength of the cable assembly 10. As the cable loop 15 is tightened around the bone 13, the tension force acting along the cable pulls the small loop 48 in a direction perpendicular to the coupling member 16. The loop crimp member 18 secures the fixed end portion 20 of the cable under the tension load and also the portion of the cable in the crimp adjacent the fixed end. The load experienced by the small loop 48 is distributed against the coupling member 16 and the tendency of the fixed cable end 20 to pull through the loop crimp member 18 is diminished.

Figure 7:
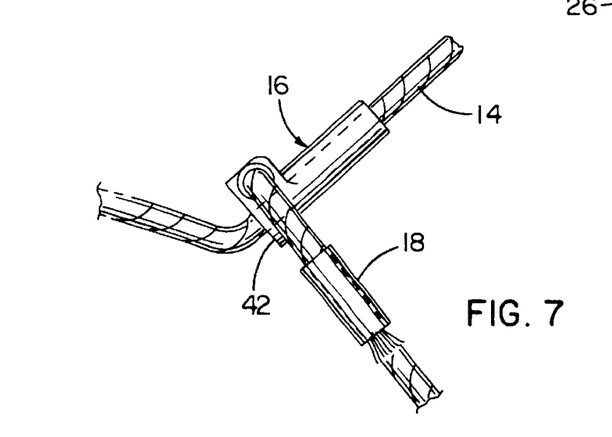
FIG. 7 is a fragmentary side elevational view of the surgical cable assembly of FIG. 4, with the free end of the cable passed through the crimp able coupling member, illustrating engagement of the loop crimp by the flange of the crimp able coupling member.

The coupling member 16 also may comprise an exterior flange 42 to limit rotation of the small loop 48. The flange 42 is located adjacent the second end 31 of the coupling member 16 and extends beneath the small cable loop 48 as shown in FIG. 7. Referring to FIGS. 3 and 7, the flange 42 limits rotation of the coupling member in a direction away from the loop crimp member 18. Limiting rotation of the coupling member increases ease of installation during the surgical procedure. In this respect, the flange 42 helps to maintain the desired configuration of the surgical cable assembly 10 described above at all times so that the surgeon is not required to flip the coupling member 16 about the small loop 48 to ensure that the small loop 48 encircles the neck portion 24 prior to threading the cable 14 through the aperture 26. As shown in FIGS. 5 and 6, the flange 42 projects outward from the wall 29 of the neck portion 24 and extends partially around the outer circumference of the neck portion 24. The flange 42 extends outward a sufficient distance so that face 50 engages the small loop 48 to limit further rotation of the coupling member away from the loop crimp 18.

The present invention also eases installation because, as shown in FIGS. 1 and 4, the small loop 48 holds the coupling member 16 in generally the same plane as loop crimp 18 and the larger cable loop 15. This makes it easier for the surgeon to locate the aperture 26 and thread the free end 22 of the cable through the aperture 26.

Although the advantages of locating the coupling member on a small cable loop should now be apparent, the invention encompasses other means of rotatably mounting the coupling member on the cable. Thus, for example, a pair of stops secured to the cable 14 at opposite sides of the shoulder aperture 40 may locate the coupling member 16 for rotation about the cable without the use of a small permanent loop 48. Other mechanisms for rotatably mounting the coupling member 16 may also be used.

Figure 8:
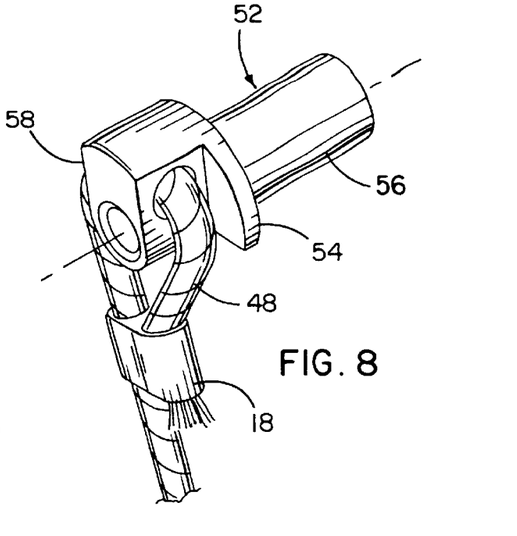
FIG. 8 is a perspective view of a crimp able coupling member and loop crimp in accordance with a second embodiment of the present invention.
Figure 9:
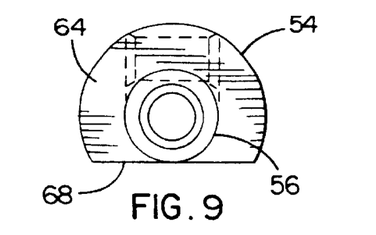
FIG. 9 is a front end elevational view of the crimp able coupling member of FIG. 8.
Figure 10:
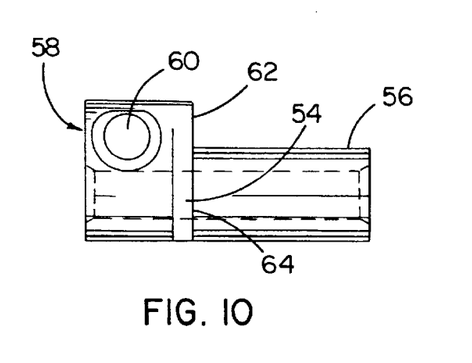
FIG. 10 is a left side elevational view of the crimp able coupling member of FIG. 8.

Referring now to FIGS. 8–10, there is illustrated a second embodiment in accordance with the present invention. The surgical cable assembly of the second embodiment is the same as described above and shown in FIGS. 1–7, with the exception of the coupling member, which utilizes a flange of different shape and configuration.

More particularly, a flange 54 extends from the neck portion 56 of the coupling 52 toward the loop crimp member 18 between shoulder aperture 60 and the front wall 62 of the shoulder portion 58. In the disclosed embodiment, the outer face 64 of the flange 54 is flush with the front wall 62. The flange 54 extends radially from the neck portion 56 and has a radius of curvature that rotates about the central longitudinal axis of the neck portion 56. As best shown in FIG. 9, the flange 54 terminates at edge 68 which lies in a plane tangent to the neck portion 56.

Figures 20A, 20B:
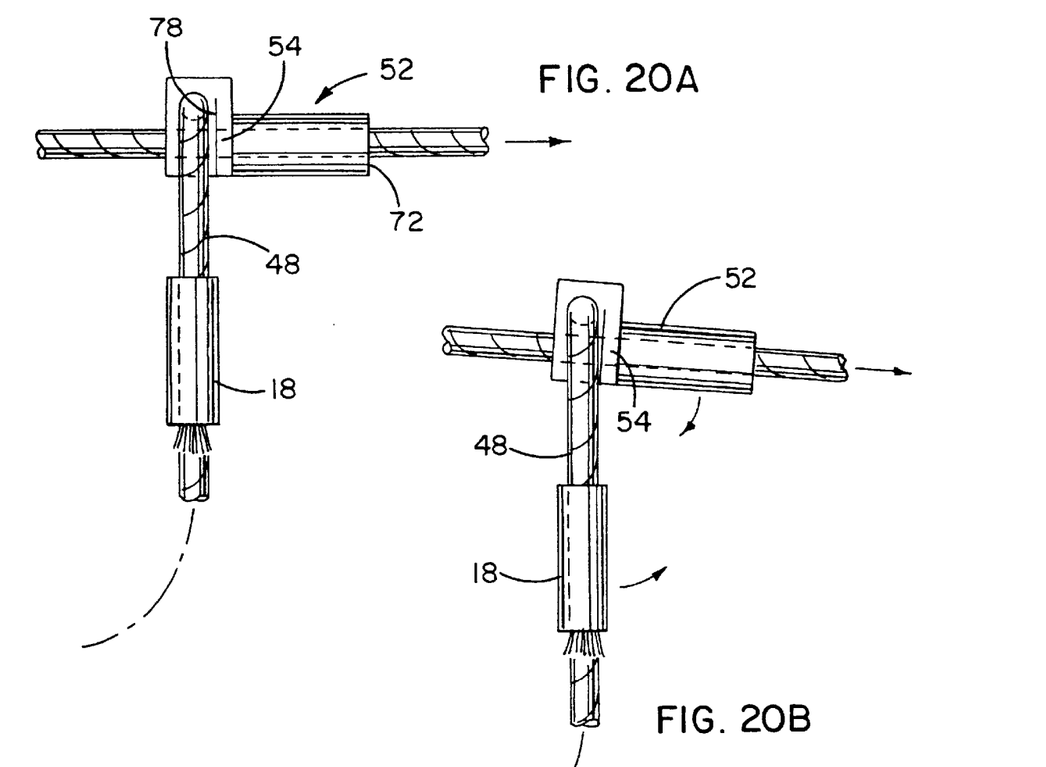
FIG. 20A is a fragmentary side elevational view of the surgical cable assembly of FIG. 8 showing the crimp able coupling member and the loop crimp, with the free end of the cable looped through the crimp able coupling member.
FIG. 20B is a view similar to FIG. 20A but showing the crimp able coupling member rotating toward the loop crimp.
Figure 20C:
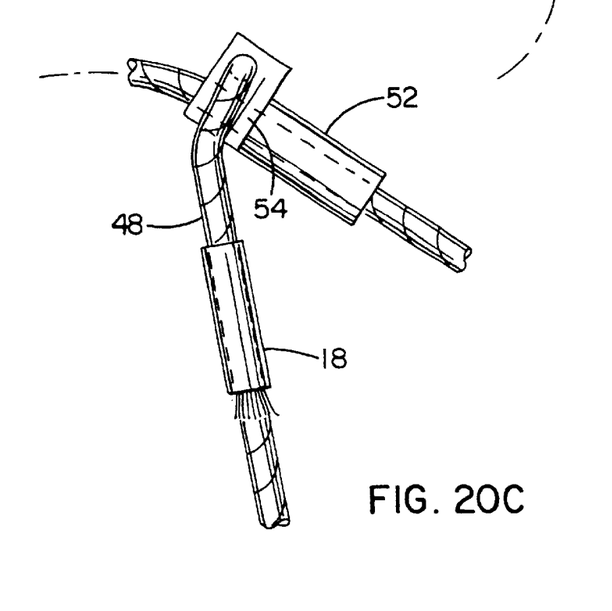
FIG. 20C is a view similar to FIG. 20B but showing increased rotation of the crimp able coupling member toward the loop crimp.

With the flange 54 positioned between the aperture 60 and the front wall 62, it may serve to control the degree of rotation of the coupling member 52 toward loop crimp member 18, as shown in FIGS. 20A–20C. As the coupling member 52 rotates toward the crimp member 18, the interior face 78 of the flange 54 engages the small loop 48. Further rotation of the coupling member 52 causes the small loop 48 to flex about the flange 54 (FIG. 20C). Thus, by use of a flange member located above the small loop crimp, the degree of rotation may be controlled if desired, for example, to prevent the neck portion of the coupling member from engaging the separate loop crimp. The amount of rotation permitted will depend on the size of the flange, the spacing of the flange relative to the aperture 60, and the flexibility of the small cable loop 48. The greater the stiffness of the small loop 48, the more the flange 54 will tend to maintain the coupling member 52 and the crimp member 18 in spaced relation.

The remaining features of the coupling member 52 may be as described above for the coupling member 16 of FIGS. 1–7.

Figures 11, 12, 13:
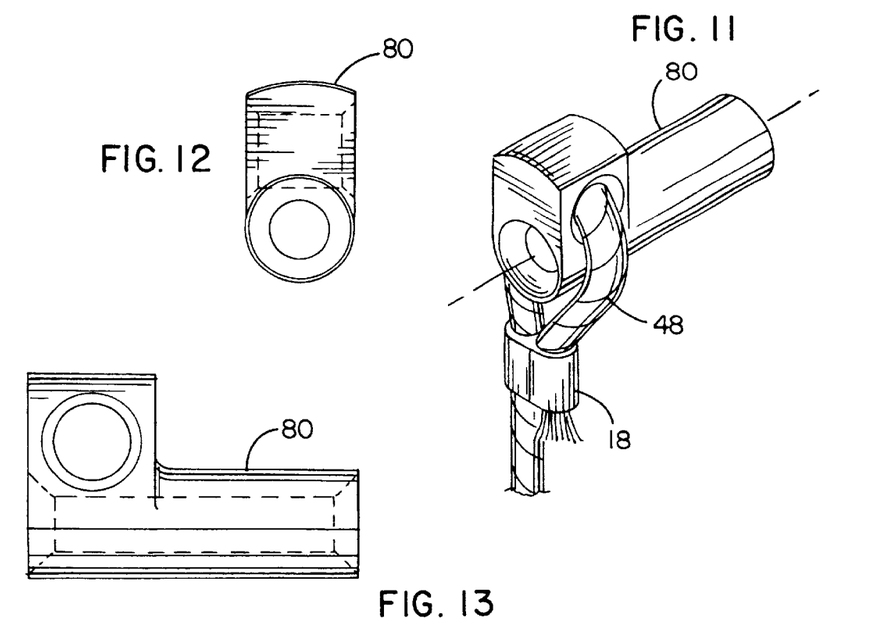
FIG. 11 is a perspective view of a crimp able coupling member and loop crimp in accordance with a third embodiment of the present invention.
FIG. 12 is a front end elevational view of the crimp able coupling member of FIG. 11.
FIG. 13 is a left side elevational view of the crimp able coupling member of FIG. 11.

Referring now to FIGS. 11–13, there is illustrated a third embodiment in accordance with the invention. The surgical cable assembly of the third embodiment is the same as described above and shown in FIGS. 1–6, with the exception of the coupling member. More particularly, the coupling member 80 of the third embodiment does not include a flange. Thus, the coupling member 80 is free to rotate about the small loop 48 in either direction. The remaining features of the coupling member 80 may be as described above for the coupling member 16 shown in FIGS. 1–7.

Figures 14, 15, 16:
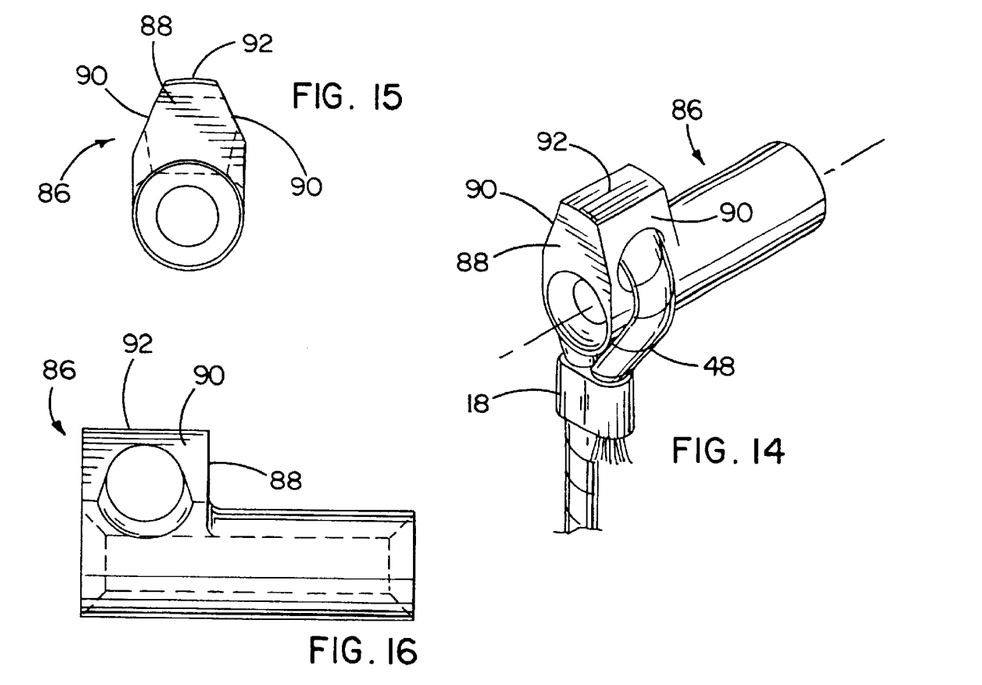
FIG. 14 is a perspective view of a crimp able coupling member and loop crimp in accordance with a fourth embodiment of the present invention.
FIG. 15 is a front end elevational view of the crimp able coupling member of FIG. 14.
FIG. 16 is a left side elevational view of the crimp able coupling member of FIG. 14.

Referring now to FIGS. 14–16, there is illustrated a fourth embodiment in accordance with the invention. The surgical cable assembly of the fourth embodiment is the same as described above and shown in FIGS. 1–6, with the exception of the coupling member. More particularly, the coupling member 86 of the fourth embodiment does not include a flange. Thus, the coupling member 86 is free to rotate about the small loop 48 in either direction. The shoulder portion 88 also differs in that the side walls 90 taper inward up to the top wall 92, thereby reducing the overall size of the shoulder portion 88. The remaining features of the coupling member 86 may be as described above for the coupling member 16 shown in FIGS. 1–7.

Figures 17, 18, 19:
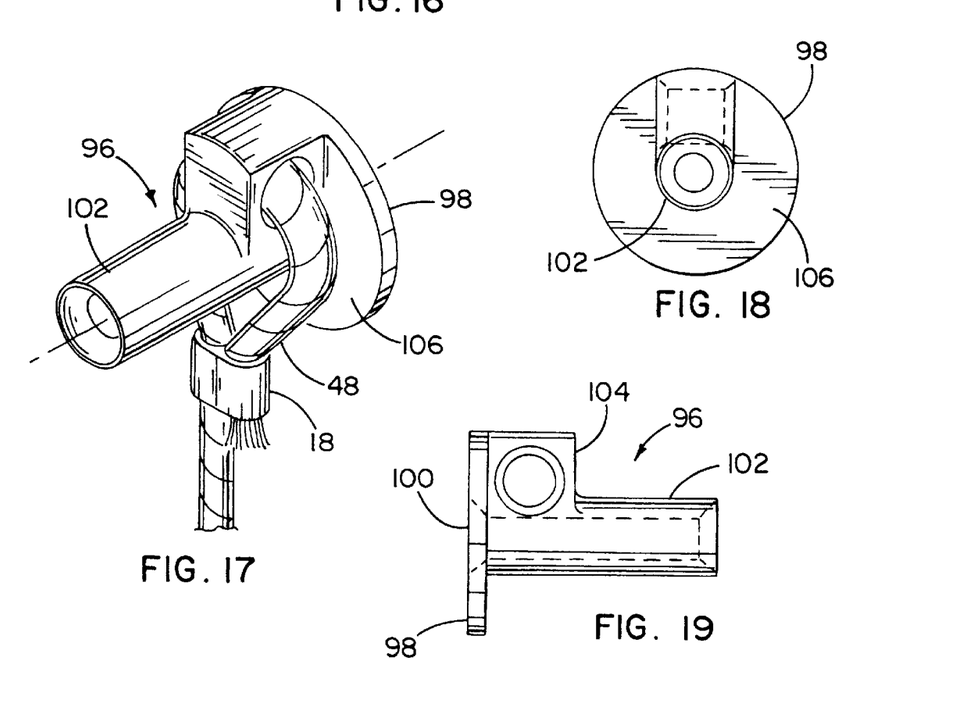
FIG. 17 is a perspective view of a crimp able coupling member and loop crimp in accordance with a fifth embodiment of the present invention.
FIG. 18 is a front end elevational view of the crimp able coupling member of FIG. 17.
FIG. 19 is a left side elevational view of the crimp able coupling member of FIG. 17.

Referring now to FIGS. 17–19, there is illustrated a fifth embodiment in accordance with the invention. The surgical cable assembly of the fifth embodiment is the same as described above and shown in FIGS. 1–6, with the exception of the coupling member. With the coupling member 96 of the fifth embodiment, the shape of the flange 98 differs. More particularly, the flange 98 is in the form of a circular disk adjacent the shoulder end 100 of the coupling member 96. The circular flange 98 has a radius that rotates about the central longitudinal axis of the neck portion 102 and extends outward a distance generally equal to the height of the shoulder portion 104. Thus, as the coupling member 96 rotates, the interior face 106 of the flange 98 engages the small loop 48 to limit further rotation.

For the sake of brevity, the method of the invention is described with primary reference to the first embodiment described above. In accordance with the method of the present invention, the cable assembly 10 is installed around a bone during a surgical procedure. The cable assembly 10 is preferably pre-assembled at the factory so that the coupling member 16 is rotatably attached to the small cable loop 48, so that the surgeon need not handle loose pieces. In embodiments where the coupling member 16 includes a flange 42 at the shoulder end 31 that prevents rotation of the small loop 48 around the end 31 of the coupling member 16, the surgeon need not be concerned with adjusting the configuration of the cable assembly 10 during the surgical procedure.

When the surgical site is identified and prepared, the surgeon passes the free end 22 of the cable 14 around the bone. If desired, the cable 14 may be passed around the bone with the assistance of a separate tool known as a "cable passer," as is known in the art. The method further entails threading the free end 22 that has been passed around the bone through the aperture 26 of the coupling member 16, from the second end 31, through the neck, and out the first end 30 in the direction of arrow A (FIG. 2). In this manner, the loop 15 is loosely positioned around the bone 12 at the surgical site. The method may include first adjusting the orientation of the coupling member to provide a convenient angle of entry of the cable based on the space limitations of the surgical site.

After being passed through the coupling member 16, the free end 22 of the cable 14 may be connected to the desired tensioning tools to further draw the cable 14 through the coupling member 16 and achieve a desired tension in the loop 15. The cable loop 15 may be tightened using any tensioning tool known to those skilled in the art, such as disclosed in U.S. Pat. Nos. 4,966,600 and 5,116,340, incorporated by reference herein. To minimize slack in the resulting loop 15, the cable is tension ed to a such an extent that the coupling member 16 rotates about the small loop 48 so that the cable 14 and coupling member 16 lie more flush with the surface of the bone. A temporary holding device as is known in the art may be used to maintain the surgical cable assembly at the desired tension while one or more other surgical cable assemblies are installed at the surgical site. The tensioning tool then may again be used to adjust the tension in the surgical cable assembly as necessary.

When the desired tension is achieved, the neck portion 24 is crimped to permanently hold the coupling member 16 at that position along the length of cable 14 to maintain the desired level of tension in the loop 15. The cable 14 is then cut generally flush with the first end 30 of the coupling member 16 and is thus permanently positioned around the bone at the surgical site. In practicing the method, the degree of allowable rotation and, thus, the final orientation of the coupling member relative to the bone surface may be controlled by engagement of a flange extending from the coupling member with the surface of the small loop opposite the bone surface.

It should be understood that if it is desired to secure an implant device or graft and a bone or two bones together with the surgical cable assembly 16, the installation of the cable is completed in a similar manner.

Numerous alternatives, modifications and variations of the surgical cable assembly are possible to improve the use and method of installing a surgical cable in accordance with the present invention. Thus, modifications and variations in the practice of the invention are expected to be apparent to those skilled in the art after consideration of the foregoing detailed description of the invention. Although preferred embodiments have been described above and illustrated in the accompanying drawings, there is no intent to limit the scope of the invention to these or any other particular embodiments. Consequently, any such modifications and variations are intended to be included within the scope of the following claims, which further describe and point out the invention.

What is claimed is:

1. A surgical cable assembly comprising:
   a cable having a pair of stops;
   a first crimp member having a first aperture defining a pivot axis extending therethrough and receiving a first portion of said cable between said stops, and a crimpable portion having a second aperture for receiving a second portion of said cable spaced from said stops by a length of cable encircling a bone;
   said stops locating and keeping the crimp member on the cable as the second cable portion is inserted through the second aperture during a surgical procedure, wherein the first crimp member is rotatably mounted on the first cable portion received in the first aperture for pivoting about the pivot axis thereof.

2. A surgical cable assembly comprising:
   a cable having a pair of stops;
   a first crimp member having a first aperture receiving a first portion of said cable between said stops, and a crimpable portion having a second aperture for receiving a second portion of said cable spaced from said stops by a length of cable encircling a bone;
   said stops locating the crimp member on the cable, wherein the first crimp member is rotatably mounted on the axis of the first cable portion received in the first aperture and the first and second stops are portions of a second crimp member and an end of the cable is fixed in said second crimp to form a cable loop which extends through the first aperture.

3. The surgical cable assembly of claim 2 wherein the first and second apertures have nonintersecting perpendicular longitudinally extending axis.

4. The surgical cable assembly of claim 2 wherein said crimpable portion comprises a malleable material configured to be compressed about the second portion of said cable for fixing the crimp member to the cable and thereby securing the cable assembly around the bone.

5. A surgical cable assembly comprising:
a cable having a pair of stops;
a first crimp member having a first aperture receiving a first portion of said cable between said stops, and a crimpable portion having a second aperture for receiving a second portion of said cable spaced from said stops by a length of cable encircling a bone;
said stops locating the crimp member on the cable, wherein the first crimp member is rotatably mounted on the axis of the first cable portion received in the first aperture and the first and second stops are separate crimps attached to the cable on the opposite sides of said first aperture.

6. A surgical cable assembly comprising:
a cable having a pair of stops;
a first crimp member having a first aperture receiving a first portion of said cable between said stops, and a crimpable portion having a second aperture for receiving a second portion of said cable spaced from said stops by a length of cable encircling a bone;
said stops locating the crimp member on the cable, wherein the first crimp member is rotatably mounted on the axis of the first cable portion received in the first aperture and wherein the crimp includes a flange to limit rotation of the crimp member in a direction.

7. A surgical cable assembly for encircling a bone comprising:
a coupling member comprising:
a first part having a first aperture extending therethrough; and
a second part having a crimpable portion and a second aperture extending through the crimpable portion;
a flexible cable having first and second end portions with the first end portion comprising a pivot loop that extends through the first aperture for pivoting therein to allow the second end portion of the cable to be pulled through the second aperture for drawing the cable tight about a bone with pivoting of the loop minimizing bending of the cable.

8. The surgical cable assembly of claim 7 wherein the first and second apertures have nonintersecting longitudinally extending central axes perpendicular to one another.

9. The surgical cable assembly of claim 7 wherein the loop extends around an outer surface of the coupling member.

10. The surgical cable of claim 7 wherein the coupling member further comprises a flange for limiting rotation of the crimpable portion of the coupling member toward the fastener.

11. The surgical cable assembly of claim 7 wherein the coupling member further comprises a flange for limiting rotation away from the fastener.

12. The surgical cable assembly of claim 7 wherein the flexible cable comprises a multistrand metal cable.

13. The surgical cable assembly of claim 7 wherein the cable has a predetermined diameter and the first aperture has a predetermined clearance diameter that is larger than the cable diameter to allow for substantially free rotation of the loop in the first aperture.

14. A method of securing a bone with a surgical cable assembly comprising:
providing a surgical cable assembly comprising a coupling member having a first part with a first aperture extending therethrough, as second part having a second aperture extending therethrough, and a flexible cable having first and second ends spaced by a length, the coupling member rotatably mounted at the second aperture about the cable adjacent the second end;
passing the first end of the cable around the bone to form a loop around the bone;
passing the first end of the cable through the first aperture;
applying a desired tension on the cable loop and thereby causing the coupling member to rotate about a portion of the cable extending through the second aperture; and
fixing the coupling member onto the portion of cable residing in the first aperture to secure the surgical cable assembly around the bone at the desired tension.

15. The method of claim 14 further comprising utilizing a tensioning tool to tighten the loop to the desired tension.

16. The method of claim 14 further comprising cutting the flexible cable essentially flush with the end of the second part of the coupling member.

17. The method of claim 14 further comprising passing the flexible cable around a medical implant positioned adjacent the bone for securing the medical implant against the bone.

18. A method of securing a bone with a surgical cable assembly comprising:
providing a surgical cable assembly comprising a coupling member having a first part with a first aperture extending therethrough, a second part having a second aperture extending therethrough, and a flexible cable having first and second ends spaced by a length the coupling member rotatably mounted at the second aperture about the cable adjacent the second end;
passing the first end of the cable around the bone to form a loop around the bone;
passing the first end of the cable through the first aperture;
applying a desired tension on the cable loop and thereby causing the coupling member to rotate about the cable; and
fixing the coupling member about the portion of cable residing in the first aperture to secure the surgical cable assembly around the bone at the desired tension, wherein the coupling member is rotatably mounted about the cable by passing the second end through the second aperture and securing the second end back against a length of the cable to form a loop.

19. The method of claim 18 wherein the second cable end is secured by crimping a tubular sleeve member about the second end and the length of flexible cable.

20. A surgical cable assembly comprising:
a cable having opposite end portions;
a coupling member for being secured to one of the cable end portions;
a fastener secured to the other cable end portion spaced from the coupling member to allow pivoting of the coupling member relative to the fastener;
a pivot portion of the coupling member having a pivot axis about which the other cable end portion pivots; and a crimp portion of the pivot coupling member including an aperture through which the one end portion of the cable is pulled causing pivoting of the coupling member toward the fastener to allow the cable to be drawn tightly about a bone surface in substantial conformance therewith.

21. The surgical cable assembly of claim 20 wherein the pivot portion of the coupling member includes an aperture through which the pivot axis extends.

22. The surgical cable assembly of claim 20 wherein the fastener comprises a crimp member spaced from the coupling member to allow the coupling member including the crimp portion and one cable end portion to pivot toward the crimp member upon pulling of the one cable end portion through the aperture of the coupling member crimp portion.

* * * * *